(12) United States Patent
Collins

(10) Patent No.: US 9,040,472 B2
(45) Date of Patent: May 26, 2015

(54) SKIN CLEANSING SYSTEM AND METHOD

(75) Inventor: Frank Collins, Lincoln (CA)

(73) Assignee: University of New Brunswick, Fredericton, New Brunswick (CA)

( * ) Notice: Subject to any disclaimer, the term of this patent is extended or adjusted under 35 U.S.C. 154(b) by 0 days.

(21) Appl. No.: 13/481,335

(22) Filed: May 25, 2012

(65) Prior Publication Data

US 2012/0231988 A1 Sep. 13, 2012

Related U.S. Application Data

(63) Continuation of application No. 12/698,766, filed on Feb. 2, 2010, now abandoned.

(51) Int. Cl.
 *C11D 3/20* (2006.01)
 *A61Q 19/10* (2006.01)
 *A61K 8/37* (2006.01)

(52) U.S. Cl.
 CPC .. *A61K 8/37* (2013.01); *A61Q 19/10* (2013.01)

(58) Field of Classification Search
 CPC .......... A61Q 19/10; A61K 8/463; A61K 8/37
 USPC ................................................. 510/125, 159
 See application file for complete search history.

(56) References Cited

U.S. PATENT DOCUMENTS

| | | | | |
|---|---|---|---|---|
| 5,466,719 A * | 11/1995 | Jakobson et al. | | 514/785 |
| 6,114,290 A * | 9/2000 | Lyle et al. | | 510/120 |
| 6,120,783 A * | 9/2000 | Roe et al. | | 424/402 |
| 6,147,120 A * | 11/2000 | Swart et al. | | 514/721 |
| 6,551,602 B1 * | 4/2003 | Barrett et al. | | 424/401 |
| 6,939,552 B2 * | 9/2005 | Ansara et al. | | 424/401 |
| 7,410,937 B2 * | 8/2008 | Grascha et al. | | 510/130 |
| 7,612,027 B2 * | 11/2009 | Grasha et al. | | 510/130 |
| 2004/0167479 A1 * | 8/2004 | Warren et al. | | 604/289 |
| 2004/0191330 A1 * | 9/2004 | Keefe et al. | | 424/638 |
| 2004/0228824 A1 * | 11/2004 | Voigt et al. | | 424/70.16 |
| 2004/0247531 A1 * | 12/2004 | Riedel et al. | | 424/47 |
| 2004/0247552 A1 * | 12/2004 | Blin et al. | | 424/70.13 |
| 2006/0039886 A1 * | 2/2006 | Shefer et al. | | 424/73 |
| 2006/0073110 A1 * | 4/2006 | Modi | | 424/70.13 |
| 2007/0275021 A1 * | 11/2007 | Lee et al. | | 424/401 |
| 2007/0297999 A1 * | 12/2007 | Fonolla Moreno et al. | | 424/59 |
| 2008/0057014 A1 * | 3/2008 | Masuda et al. | | 424/64 |
| 2008/0107697 A1 * | 5/2008 | Blin et al. | | 424/401 |

* cited by examiner

*Primary Examiner* — Nicole M Buie-Hatcher
*Assistant Examiner* — M. Reza Asdjodi
(74) *Attorney, Agent, or Firm* — Eugene F. Derényi; Fogler, Rubinoff LLP

(57) ABSTRACT

A cleansing composition for cleansing skin, especially for removing grease from skin. A cleaning composition of the present invention may also be used in ready-to-use (or in-use) kits, such as two component kits, suitable for cleansing skin.

17 Claims, No Drawings

SKIN CLEANSING SYSTEM AND METHOD

CROSS-REFERENCE TO RELATED APPLICATIONS

This application is a continuation of U.S. patent Ser. No. 12/698,766 filed on Feb. 2, 2010 (currently pending), which is incorporated herein by reference in its entirety.

FIELD OF THE INVENTION

The present invention relates to skin cleansers in general and environmentally-friendly skin cleansers in particular.

BACKGROUND OF THE INVENTION

A solvent is a liquid or gas that dissolves a solid, liquid, or gaseous solute, resulting in a solution. Water is the most commonly used solvent for everyday cleansing of skin. Water alone, however, is usually insufficient to remove non-water soluble substances such as oil-based paint, grease, oil, non-water based glue, and the like from skin. Products such as for example Varsol™ and mineral spirits can remove such substances from skin but are toxic to animals, humans and the environment generally, and they cannot be disposed of safely in municipal water systems. Such prior art solvents often contain known carcinogens such as toluene and benzene which can be hazardous to health through prolonged exposure to the skin. As many of these solvents are also highly volatile, they emit harmful vapors, making them flammable and difficult to store safely.

Increasingly, there is a desire and need for more environmentally-friendly skin cleansers. A cleanser which is "environmentally-friendly" is one which is generally benign to the environment and human health in particular.

SUMMARY OF THE INVENTION

In one aspect, the present invention relates to a solvent that can be applied freely to skin and removed with a solvent remover and water.

In another aspect, the present invention relates to a solvent which is non-phosphate-based, biodegradable, non-miscible in water, and environmentally-friendly, and a separate solvent remover which is environmentally-friendly.

In a further aspect, the present invention relates to a solvent which is non-toxic and non-hazardous to human health and has a high flashpoint (meaning it is much less volatile than petroleum-based solvents) and a solvent remover distinct from the solvent, where the solvent remover is a surfactant, such as a non-ionic surfactant.

In a still further aspect, the present invention relates to a non-aqueous solvent component and a solvent remover component which is separate from the solvent component until applied to the solvent component to remove the solvent component from a surface.

In a still further aspect, the present invention relates to a two component skin cleansing system comprising bio-alkyl ester as a first component and a surfactant as a second component where the first and second components are uncombined.

In a still further aspect, the present invention relates to a skin cleansing system comprising a solvent and a separate and distinct solvent remover. The solvent is derived from one or more vegetable or animal saturated and/or unsaturated fatty acids from one or more natural sources. Examples of natural sources of vegetable saturated and/or unsaturated fatty acids include vegetable oils from oil-seed plants such as sunflower seed oil, soybean oil, canola seed oil, cotton oil, corn oil, peanut oil or coconut oil. Examples of animal saturated and/or unsaturated fatty acids include fish oils from aquacultured fish such as aquacultured salmon.

In a further aspect, the present invention relates to a skin cleansing system comprising essentially of a solvent and a separate and distinct solvent remover, where the solvent is derived from at least one of an agricultural feedstock oil or an aquacultural feedstock oil and the solvent remover is a non-ionic surfactant, an "oxy"-based surfactant or a soap or detergent which includes an oxy-based surfactant.

In a further aspect, the present invention relates to a skin cleansing system comprising essentially of a bio-alkyl ester and a separate and distinct solvent remover, where the solvent remover is a non-ionic surfactant or oxy-based soap.

In a further aspect, the present invention relates to a skin cleansing system comprising a: (i) non-water miscible solvent derived from a natural source; and (ii) a solvent remover, wherein the solvent and the solvent remover are not combined prior to use.

In yet a further aspect, the present invention relates to a kit for cleansing skin comprising: a first component comprising a non-water miscible solvent derived from a natural source and a second component separate from the first component comprising a solvent remover.

In another aspect, the present invention relates to a method comprising: providing a non-water miscible solvent derived from a natural source, providing a solvent remover, applying the solvent to skin, then applying the solvent remover to the skin to remove at least some of the applied solvent, and rinsing the skin with water.

DETAILED DESCRIPTION OF THE INVENTION

A cleansing system embodying the principles of the present invention may be used as a cleanser, and in particular, a skin cleanser, especially for removing grease or oil from skin. A cleansing system of the present invention may also be used in ready-to-use (or in-use) kits, such as two component kits, suitable for cleansing skin.

In one embodiment, the cleansing system of the present invention comprises: (i) a solvent which is non-miscible in water; and (ii) a separate solvent remover. The solvent is for subsequent application to a surface to cleanse it and the solvent remover is for application to the surface to remove the applied solvent.

The solvent can be an alkyl ester derived from a natural source and the solvent remover can be a surfactant, an oxy-based soap or detergent in aqueous solution that can remove the solvent from skin.

The alkyl ester can be selected from the group consisting of methyl esters, ethyl esters, propyl esters, and butyl esters. Suitable methyl esters can be selected from the group consisting of hexadecanoic acid methyl ester (methyl palmitate); pentadecanoic acid; 14-methyl-methyl ester; 9,12-octadecadienoic acid methyl ester (methyl linoleate); 8,11-Octadecadienoic acid methyl ester; methyl oleate; methyl cis-9-octadecenoate; octadecanoic acid methyl ester (ethyl stearate); 9-Hexadecenoic acid methyl ester (Palmitoleic Acid methyl; 13-docosenoic acid methyl ester; (Z)—(Erucic acid methyl ester); tetracosanoic acid methyl ester (methyl tetracosanoate); heneicosanoic acid methyl ester eicosanoic acid methyl ester (methyl arachidate; methyl eicosanoate) and heneicosanoic acid methyl ester.

The solvent can consist essentially of one or more alkyl esters. However, when the solvent is an alkyl ester derived from a natural source using a conventional trans-esterification process, the solvent will typically also include one or more by-products from the trans-esterification process such as fatty acids from the natural source. One or more additives can also be naturally present in the solvent. For example, if an alkyl alcohol is used in the trans-esterification process, residual alkyl alcohol from the process may be present in the solvent and can serve as a stabilizer.

Other additives can be added to the solvent. When the solvent is for cleansing skin, an additive may be selected from the group consisting of lanolin, linoleic acid and lauric acid and combinations thereof because of their beneficial properties on skin. Additives can also include one or more additives selected from the group consisting of an antioxidant, a pour depressant, a colourant, a fragrance and a stabilizer. An example of an antioxidant which can be used is Ionol CP (Butylated Hydroxytoluene) from Evonik Degussa Industries. The stabilizer is one which helps prevent degradation of the cleaning compositions with prolonged storage and, as discussed above, can for example be an alkyl or methyl alcohol. If for example alkyl alcohol is "left over" from the trans-esterification process used to make the solvent, the alkyl alcohol can serve as the stabilizer.

The solvent remover may be a surfactant such as a non-ionic surfactant. The non-ionic surfactant can be selected from the group consisting of alcohol ethoxylate, alkylpolyglycoside, fatty alcohol amide, and amine oxide. The solvent remover can also be a polyoxyolefin group product alone or in combination with a sulphate or sulfonate anionic surfactant. The solvent remover may also be a phosphate-based or non-phosphate-based soap, oxy-based soap or detergent. A soap or detergent comprising an oxy-based surfactant has been found to be a particularly effective solvent remover. The solvent remover may further include one or more "oxide"-based additives, such as those selected from the group consisting of sodium carbonate, sodium percarbonate and a perhydrated compound.

Additives that are not environmentally-friendly or are hazardous to human health generally, or are an irritant to skin should not be included in the compositions of the present invention.

In a non-limiting example, Table 1 sets out components of an example of a solvent component of a cleansing system according to one embodiment of the present invention in which the solvent component comprises a bio-alkyl ester, an antioxidant and a pour depressant. The bio-alkyl ester is generally non-toxic to human skin when used as directed and is derived from an agricultural-based oil using conventional processes known to those of ordinary skill in the art. The bio-alkyl ester comprises methyl esters listed in Table 1 under the heading "Methyl Esters", as well as the fatty acids listed in Table 1 under the heading "Fatty Acids". It will be understood by those of ordinary skill in the art that the composition of bio-alkyl ester usable as the solvent in the present invention can vary depending upon the feedstock source used for the bio-alkyl ester. The bio-alkyl ester will typically comprise one or more methyl esters and one or more fatty acids.

Lauric acid (dodecanoic acid) in the composition of Table 1 is a saturated fatty acid with a 12-carbon chain.

Linoleic acid in the composition of Table 1 is an unsaturated omega-6 fatty acid. Chemically, it is a carboxylic acid with an 18-carbon chain and two cis double bonds.

The antioxidant in the composition of Table 1 is Ionol CP (Butylated Hydroxytoluene) from Evonik Degussa Industries but it will be understood by one of ordinary skill in the art that other suitable antioxidants can be used.

The weight percentage values provided in Table 1 are approximate and sum to approximately 100%. It will be understood that the weight percentages given in Table 1 are not limiting. Alkyl esters in solvent components according to the present invention can comprise from about 60 weight % to about 100 weight % of the solvent component, with the balance being composed of fatty acids and/or additives as set out herein.

TABLE 1

| Chemical Composition of solvent component | EXAMPLE #1 wt % | EXAMPLE #2 wt % |
|---|---|---|
| Methyl Esters | | |
| Hexadecanoic acid; methyl ester (methyl palmitate) or Pentadecanoic acid; 14-methyl-methyl ester; | 7.59 | 8.27 |
| 9,12-Octadecadienoic acid; methyl ester (methlyl linoleate) or 8,11-Octadecadienoic acid; methyl ester and/or Methyl Oleate; Methyl cis-9-Octadecenoate | 74.59 | 81.04 |
| Octadecanoic acid; methyl ester (ethyl stearate) | 3.60 | 3.95 |
| 9-Hexadecenoic acid, methyl ester (Palmitoleic Acid methyl ester) or 13-Docosenoic acid, methyl ester; (Z)-(Erucic acid methyl ester) | 1.86 | 2.03 |
| Tetracosanoic acid, methyl ester (methyl tetracosanoate) or Heneicosanoic acid; methyl ester | 0.96 | 1.05 |
| Eicosanoic acid; methyl ester (methyl arachidate; methyl eicosanoate) or heneicosanoic acid; methyl ester | 0.42 | 0.46 |
| Antioxidant | 0.10 | 0.20 |
| Pour depressant | 1.00 | 2.00 |
| Fatty Acids | | |
| n-Dodecanoic acid (Lauric Acid); Dodecylic acid; Dodecoic acid | 1.00 | 0.30 |
| Oleic Acid | 2.427 | 0.132 |
| Linoleic Acid | 3.623 | 0.415 |
| Palmitic Acid | 0.431 | 0.023 |
| Stearic Acid | 0.160 | 0.009 |
| Erucic Acid | 1.957 | 0.107 |
| Palmitoleic Acid | 0.067 | 0.004 |
| Arachidic Acid | 0.027 | 0.001 |
| Eicosenoic Acid | 0.188 | 0.010 |
| Total | 100.00 | 100.00 |

In another embodiment, the skin cleansing system of the present invention can comprise a "two bottle" system with a solvent contained in one bottle and a solvent remover contained in a separate bottle. The solvent can be applied to skin, and hands in particular, to remove dirt, grease, oil and the like followed by the application of the solvent remover to remove solvent from skin to which it is applied. It will be understood by one or ordinary skill in the art that any suitable bottles can be used to contain each of the solvent and the solvent remover. The bottle for the solvent should be such that the solvent will not degrade it. Examples of suitable material for the bottles for the solvent include glass and Class 7 plastics such as nylon, ABS, acrylic, fibreglass, polycarbonate or polylactic acid, and the like and fluorine-treated HDPE but this list should not be considered as limiting.

In another embodiment, the cleaning composition of the invention comprises food-grade components. In such case, the solvent comprises one or more alkyl esters are derived from agricultural products which can be consumed by humans, using conventional processes known to those of ordinary skill in the art.

In one aspect, the invention relates to a cleansing kit suitable for cleaning human skin. A kit of the present invention may consist of the solvent component and the solvent remover component contained in separate dispensers. The dispensers can be any number of conventional dispensers such as pump dispensers or squeeze bottles. The solvent component can comprise any of the solvents suitable for the present invention as set out herein, including for example, a bio-alkyl ester. The solvent remover can comprise the solvent removers set out herein, including for example a surfactant such as a non-ionic surfactant.

In another aspect, the invention relates to a method comprising: providing a non-water miscible solvent derived from a natural source, providing a solvent remover, applying the solvent to skin, then applying the solvent remover to the skin to remove at least some of the applied solvent, and rinsing the skin with water to remove at least some of the solvent and solvent remover. The solvent component can comprise any of the solvents suitable for the present invention as set out herein, including for example, a bio-alkyl ester. The solvent remover can comprise the solvent removers set out herein, including for example a surfactant such as a non-ionic surfactant.

What is claimed is:

1. A skin cleansing system comprising:
   (i) a non-aqueous solvent component for application to skin, comprising a non-water miscible biodegradable solvent, the solvent comprising an alkyl ester derived from a natural source, the alkyl ester at a concentration of about 100 weight % of the solvent component; and,
   (ii) a solvent remover for removing the non-aqueous solvent component from skin, wherein the solvent component and the solvent remover are not combined prior to use.

2. The skin cleansing system of claim 1 wherein the solvent is derived from at least an agricultural or aquacultural source.

3. The skin cleansing system of claim 1 wherein the alkyl ester is propyl ester.

4. The skin cleansing system of claim 1 wherein the alkyl ester is a methyl ester selected from the group consisting of hexadecanoic acid methyl ester (methyl palmitate); pentadecanoic acid; 14-methyl-methyl ester; 9,12-octadecadienoic acid methyl ester (methyl linoleate); 8,11-Octadecadienoic acid methyl ester; methyl oleate; methyl cis-9-octadecenoate; octadecanoic acid methyl ester (ethyl stearate); 9-Hexadecenoic acid methyl ester (Palmitoleic Acid methyl ester); 13-docosenoic acid methyl ester; (Z)—(Erucic acid methyl ester); tetracosanoic acid methyl ester (methyl tetracosanoate); heneicosanoic acid methyl ester eicosanoic acid methyl ester (methyl arachidate; methyl eicosanoate) and heneicosanoic acid methyl ester.

5. The skin cleansing system of claim 1, wherein the solvent remover comprises a surfactant.

6. The skin cleansing system of claim 5, wherein the surfactant is a non-ionic surfactant.

7. The skin cleansing system of claim 1 wherein the solvent remover is selected from the group consisting of alcohol ethoxylate, alkylpolyglycoside, fatty alcohol amide, amine oxide and a polyoxyolefin.

8. The skin cleansing system of claim 1, further comprising lanolin.

9. The skin cleansing system of claim 1, further comprising one or more additives selected from the group consisting of an antioxidant, a pour depressant and a stabilizer.

10. A kit for cleansing skin comprising:
    a first non-aqueous solvent component for application to skin, comprising a biodegradable non-water miscible solvent, the solvent comprising an alkyl ester derived from a natural source, the alkyl ester at a concentration of about 100 weight % of the solvent component; and,
    a second component separate from the first component comprising a solvent remover for removing the non-aqueous solvent component from skin.

11. The kit of claim 10, wherein the solvent remover is a surfactant.

12. The kit of claim 10, wherein the first component further comprises lanolin.

13. The kit of claim 11, wherein the surfactant is a non-ionic surfactant.

14. The kit of claim 10 wherein the alkyl ester is propyl ester.

15. The kit of claim 10, wherein the alkyl ester is a methyl ester selected from the group consisting of hexadecanoic acid methyl ester (methyl palmitate), pentadecanoic acid, 14-methyl-methyl ester, 9,12-octadecadienoic acid methyl ester (methyl linoleate), 8,11-Octadecadienoic acid methyl ester, methyl oleate, methyl cis-9-octadecenoate, octadecanoic acid methyl ester (ethyl stearate), 9-Hexadecenoic acid methyl ester (Palmitoleic Acid methyl ester), 13-docosenoic acid methyl ester, (Z)—(Erucic acid methyl ester), tetracosanoic acid methyl ester (methyl tetracosanoate), heneicosanoic acid methyl ester eicosanoic acid methyl ester (methyl arachidate, methyl eicosanoate); heneicosanoic acid methyl ester and combinations thereof.

16. The kit of claim 10 wherein the solvent remover is selected from the group consisting of an alcohol ethoxylate, alkylpolyglycoside, fatty alcohol amide, amine oxide, a polyoxyolefin and combinations thereof.

17. The kit of claim 10, wherein the alkyl ester is a bio-alkyl ester.

* * * * *